US011679987B2

(12) United States Patent
Ojo et al.

(10) Patent No.: US 11,679,987 B2
(45) Date of Patent: *Jun. 20, 2023

(54) SSZ-91 CATALYST

(71) Applicant: Chevron U.S.A. Inc., San Ramon, CA (US)

(72) Inventors: Adeola Florence Ojo, Pleasant Hill, CA (US); Dan Xie, Richmond, CA (US); Yihua Zhang, Albany, CA (US); Guan-Dao Lei, Walnut Creek, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/317,469

(22) Filed: May 11, 2021

(65) Prior Publication Data
US 2021/0269319 A1    Sep. 2, 2021

Related U.S. Application Data

(63) Continuation of application No. 16/848,551, filed on Apr. 14, 2020, now Pat. No. 11,001,502, which is a continuation of application No. 15/753,074, filed as application No. PCT/US2016/046614 on Aug. 11, 2016, now Pat. No. 10,618,816, which is a continuation of application No. 14/837,087, filed on Aug. 27, 2015, now abandoned, and a continuation of application No. 14/837,094, filed on Aug. 27, 2015, now abandoned, and a continuation of application No. 14/837,108, filed on Aug. 27, 2015, now Pat. No. 9,920,260, and a continuation of application No. 14/837,071, filed on Aug. 27, 2015, now Pat. No. 9,802,830.

(51) Int. Cl.
| | |
|---|---|
| *B01J 29/06* | (2006.01) |
| *C01B 39/02* | (2006.01) |
| *B01J 29/74* | (2006.01) |
| *C01B 39/46* | (2006.01) |
| *B01J 29/70* | (2006.01) |
| *B01J 29/80* | (2006.01) |
| *B01J 35/00* | (2006.01) |
| *C01B 39/48* | (2006.01) |
| *B01J 29/72* | (2006.01) |
| *B01J 29/76* | (2006.01) |
| *C07C 5/13* | (2006.01) |

(52) U.S. Cl.
CPC .......... *C01B 39/023* (2013.01); *B01J 29/703* (2013.01); *B01J 29/7023* (2013.01); *B01J 29/7034* (2013.01); *B01J 29/7246* (2013.01); *B01J 29/7261* (2013.01); *B01J 29/7446* (2013.01); *B01J 29/7461* (2013.01); *B01J 29/7646* (2013.01); *B01J 29/7661* (2013.01); *B01J 29/80* (2013.01); *B01J 35/002* (2013.01); *C01B 39/46* (2013.01); *C01B 39/48* (2013.01); *C01P 2002/72* (2013.01); *C01P 2004/54* (2013.01); *C07C 5/13* (2013.01); *C07C 2529/72* (2013.01); *C07C 2529/74* (2013.01); *C07C 2529/76* (2013.01)

(58) Field of Classification Search
CPC ....... C01B 39/023; C01B 39/46; C01B 39/48; C01B 39/02; B01J 29/703; B01J 29/7023; B01J 29/7034; B01J 29/7446; B01J 29/7461; B01J 29/80; B01J 35/002; B01J 29/48; B01J 35/0006; B01J 37/0201; B01J 37/30; B01J 2229/18; B01J 2229/186; B01J 2229/20; B01J 2229/42; C01P 2004/54; C01P 2002/72; C07C 5/13; C07C 2529/72; C07C 2529/74; C07C 2529/76
USPC ...... 502/60, 63, 64, 66, 67, 68, 69; 423/701, 423/702, 704, 705, 708
See application file for complete search history.

(56) References Cited

U.S. PATENT DOCUMENTS

| | | | |
|---|---|---|---|
| 9,802,830 B2 * | 10/2017 | Ojo | B01J 29/7023 |
| 9,920,260 B2 * | 3/2018 | Ojo | C07C 5/2708 |
| 10,618,816 B2 * | 4/2020 | Ojo | B01J 29/703 |
| 11,001,502 B2 * | 5/2021 | Ojo | B01J 29/7446 |

\* cited by examiner

*Primary Examiner* — Elizabeth D Wood
(74) *Attorney, Agent, or Firm* — Mark L. Warzel

(57) ABSTRACT

A family of new crystalline molecular sieves designated SSZ-91 is disclosed, as are methods for making SSZ-91 and uses for SSZ-91. Molecular sieve SSZ-91 is structurally similar to sieves falling within the ZSM-48 family of molecular sieves, and is characterized as: (1) having a low degree of faulting, (2) a low aspect ratio that inhibits hydrocracking as compared to conventional ZSM-48 materials having an aspect ratio of greater than 8, and (3) is substantially phase pure.

15 Claims, 12 Drawing Sheets

(SSZ-91)

(SSZ-91)

(SSZ-91)

SSZ-91 CATALYST

CROSS-REFERENCE TO RELATED APPLICATIONS

This application is a continuation of U.S. patent application Ser. No. 16/848,551, filed on Apr. 14, 2020, now U.S. Pat. No. 11,001,502, and a continuation of U.S. patent application Ser. No. 15/753,074, filed on Feb. 15, 2018, now U.S. Pat. No. 10,618,816, which is a 371 (c)(1) filing based on PCT Appl. No. PCT/US2016/046614, filed on Aug. 11, 2016, and a continuation of U.S. patent application Ser. No. 14/837,071, filed on Aug. 27, 2015, now U.S. Pat. No. 9,802,830, and a continuation of U.S. patent application Ser. No. 14/837,087, filed on Aug. 27, 2015, now abandoned, and a continuation of U.S. patent application Ser. No. 14/837,094, filed on Aug. 27, 2015, now abandoned, and a continuation of U.S. patent application Ser. No. 14/837,108, filed on Aug. 27, 2015, now U.S. Pat. No. 9,920,260, all herein incorporated in their entirety.

TECHNICAL FIELD

Described herein is a new family of crystalline molecular sieves designated as SSZ-91, methods for preparing SSZ-91 and uses for SSZ-91.

BACKGROUND

Because of their unique sieving characteristics, as well as their catalytic properties, crystalline molecular sieves and molecular sieves are especially useful in applications such as hydrocarbon conversion, gas drying and separation. Although many different crystalline molecular sieves have been disclosed, there is a continuing need for new molecular sieves with desirable properties for gas separation and drying, hydrocarbon and chemical conversions, and other applications. New molecular sieves may contain novel internal pore architectures, providing enhanced selectivities in these processes.

Molecular sieves have distinct crystal structures which are demonstrated by distinct X-ray diffraction patterns. The crystal structure defines cavities and pores which are characteristic of the different species.

Molecular sieves are classified by the Structure Commission of the International Zeolite Association according to the rules of the IUPAC Commission on Zeolite Nomenclature. According to this classification, framework type zeolites and other crystalline microporous molecular sieves, for which a structure has been established, are assigned a three letter code and are described in the "Atlas of Zeolite Framework Types" Sixth Revised Edition, Elsevier (2007) and the Database of Molecular sieve Structures on the International Zeolite Association's website (http://www.iza-online.org).

The structure of a molecular sieve can be either ordered or disordered. Molecular sieves having an ordered structure have periodic building units (PerBUs) that are periodically ordered in all three dimensions. Structurally disordered structures show periodic ordering in dimensions less than three (i.e., in two, one or zero dimensions). Disorder occurs when the PerBUs connect in different ways, or when two or more PerBUs intergrow within the same crystal. Crystal structures built from PerBUs are called end-member structures if periodic ordering is achieved in all three dimensions.

In disordered materials, planar stacking faults occur where the material contains ordering in two dimensions. Planar faults disrupt the channels formed by the material's pore system. Planar faults located near the surface limit diffusion pathways otherwise required in order to allow feedstock components to access the catalytically active portions of the pore system. Therefore, as the degree of faulting increases, the catalytic activity of the material typically decreases.

In the case of crystals with planar faults, interpretation of X-ray diffraction patterns requires an ability to simulate the effects of stacking disorder. DIFFaX is a computer program based on a mathematical model for calculating intensities from crystals containing planar faults. (See, M. M. J. Treacy et al., Proceedings of the Royal Chemical Society, London, A (1991), Vol. 433, pp. 499-520). DIFFaX is the simulation program selected by and available from the International Zeolite Association to simulate the XRD powder patterns for intergrown phases of molecular sieves. (See, "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA and KFI molecular sieves, as reported by K. P. Lillerud et al. in "Studies in Surface Science and Catalysis", 1994, Vol. 84, pp. 543-550. DIFFaX is a well-known and established method to characterize disordered crystalline materials with planar faults such as intergrown molecular sieves.

The designation ZSM-48 refers to a family of disordered materials, each characterized as having a one-dimensional 10-ring tubular pore system. The pores are formed of rolled up honeycomb-like sheets of fused tetrahedral 6-ring structures, and the pore aperture contains 10 tetrahedral-atoms. Zeolites EU-2, ZSM-30 and EU-11 fall into the ZSM-48 family of zeolites.

According to Lobo and Koningsveld, the ZSM-48 family of molecular sieves consists of nine polytypes. (See, J. Am. Chem. Soc. 2002, 124, 13222-13230). These materials have very similar, but not identical, X-ray diffraction patterns. The Lobo and Koningsveld paper describes their analysis of three ZSM-48 samples provided by Dr. Alexander Kuperman of Chevron Corporation. Each of the three samples, labeled Samples A, B and C, respectively, were prepared using three different structure directing agents. Comparative Examples 2 and 3 herein below correspond to Samples A and B described in the Lobo and Koningsveld paper.

The Lobo and Koningsveld paper describes Sample A as being polytype 6, and Sample B as being a faulted polytype 6. The paper further describes the morphology of Sample A as consisting of needle-like crystals having a diameter of ~20 nm and a length of ~0.5 μm. The morphology of Sample B consisted of long, narrow crystals having a width of ~0.5 μm and a length of 4-8 μm. As indicated in Comparative Examples 2 and 3 below, the scanning electron microscopy images for Samples A and B are presented herein in FIGS. 3 and 4.

Kirschhock and co-workers describe the successful synthesis of phase-pure polytype 6. (See, Chem. Mater. 2009, 21, 371-380). In their paper, Kirschhock and co-workers describe their phase-pure polytype 6 material (which they refer to as COK-8) as having a morphology consisting of long needle-like crystals (width, 15-80 nm; length, 0.5-4 μm) with a very large length/width ratio, growing along the interconnecting pore direction.

As indicated in the Kirschhock paper, molecular sieves from the ZSM-48 family of molecular sieves consist of 10-ring, 1-dimensional pore structures, wherein the channels formed by the interconnected pores extend perpendicular to the long axis of the needles. Therefore, the channel openings are located at the short ends of the needles. As the length-to-diameter ratio (also known as aspect ratio) of these needles increases, so does the diffusion pathway for the hydrocarbon feed. As the diffusion pathway increases, so does the residence time of the feed in the channels. A longer residence time results in increased undesirable hydrocracking of the feed with a concomitant reduction in selectivity.

Accordingly, there is a current need for ZSM-48 molecular sieves which exhibit lower degree of hydrocracking over known ZSM-48 molecular sieves. There is also a continuing need for ZSM-48 molecular sieves which are phase pure or substantially phase-pure, and have a low degree of disorder within the structure (a low degree of faulting).

SUMMARY

Described herein below is a family of crystalline molecular sieves with unique properties, referred to herein as "molecular sieve SSZ-91" or simply "SSZ-91." Molecular sieve SSZ-91 is structurally similar to sieves falling within the ZSM-48 family of zeolites, and is characterized as: (1) having a low degree of faulting, (2) a low aspect ratio that inhibits hydrocracking as compared to conventional ZSM-48 materials having an aspect ratio of greater than 8, and (3) is substantially phase pure.

As will be shown in the Examples below, a ZSM-48 material lacking any one of the three uniquely combined characteristics of SSZ-91 (low aspect ratio, low EU-1 content, high polytype 6 composition) will exhibit poor catalytic performance.

In one aspect, there is provided a molecular sieve having a mole ratio of 40 to 200 of silicon oxide to aluminum oxide. In its as-made form, the X-ray diffraction lines of Table 2 herein are indicative of SSZ-91.

SSZ-91 materials are composed of at least 70% polytype 6 of the total ZSM-48-type material present in the product, as determined by DIFFaX simulation and as described by Lobo and Koningsveld in J. Am. Chem. Soc. 2012, 124, 13222-13230, where the disorder was tuned by three distinct fault probabilities. It should be noted the phrase "at least 70%" includes the case where there are no other ZSM-48 polytypes present in the structure, i.e., the material is 100% phase-pure polytype 6.

In another aspect, SSZ-91 is substantially phase pure. SSZ-91 contains an additional EUO-type molecular sieve phase in an amount of between 0 and 3.5 percent by weight (inclusive) of the total product.

Molecular sieve SSZ-91 has a morphology characterized as polycrystalline aggregates, each of the aggregates being characterized as being composed of crystallites collectively having an average aspect ratio of between 1 and 8 (inclusive). SSZ-91 exhibits a lower degree of hydrocracking than those ZSM-48 materials having a higher aspect ratio. An aspect ratio of 1 is the ideal lowest value, where the length and width are the same.

In another aspect, there is provided a method of preparing a crystalline material by contacting under crystallization conditions (1) at least one source of silicon oxide; (2) at least one source of aluminum oxide; (3) at least one source of an element selected from Groups 1 and 2 of the Periodic Table; (4) hydroxide ions; and (5) hexamethonium cations.

In yet another aspect, there is provided a process for preparing a crystalline material having, as made, the X-ray diffraction lines of Table 2, by:

(a) preparing a reaction mixture containing (1) at least one source of silicon oxide; (2) at least one source of aluminum oxide; (3) at least one source of an element selected from Groups 1 and 2 of the Periodic Table; (4) hydroxide ions; (5) hexamethonium cations; and (6) water; and (b) maintaining the reaction mixture under crystallization conditions sufficient to form crystals of the molecular sieve.

DETAILED DESCRIPTION

Introduction

Figure 1:
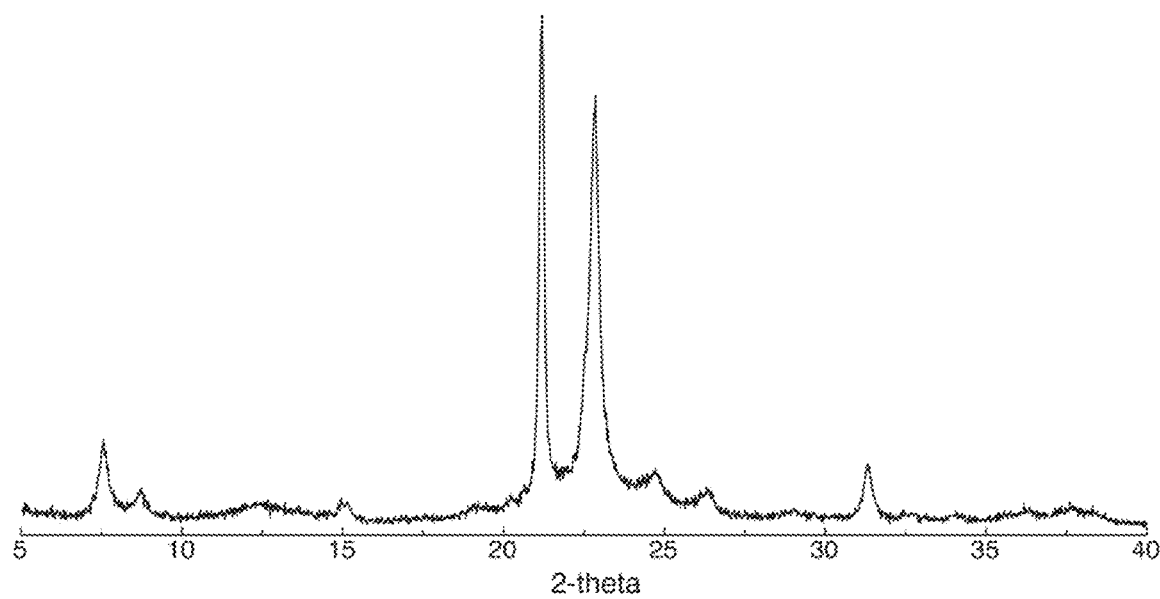
FIG. 1 is a powder X-ray diffraction (XRD) pattern of as-synthesized molecular sieve prepared in Comparative Example 1.

The term "active source" means a reagent or precursor material capable of supplying at least one element in a form that can react and which can be incorporated into the molecular sieve structure. The terms "source" and "active source" can be used interchangeably herein.

The term "molecular sieve" and "zeolite" are synonymous and include (a) intermediate and (b) final or target molecular sieves and molecular sieves produced by (1) direct synthesis or (2) post-crystallization treatment (secondary modification). Secondary synthesis techniques allow for the synthesis of a target material from an intermediate material by heteroatom lattice substitution or other techniques. For example, an aluminosilicate can be synthesized from an intermediate borosilicate by post-crystallization heteroatom lattice substitution of the Al for B. Such techniques are known, for example as described in U.S. Pat. No. 6,790,433 to C. Y. Chen and Stacey Zones, issued Sep. 14, 2004.

The term "*MRE-type molecular sieve" and "EUO-type molecular sieve" includes all molecular sieves and their isotypes that have been assigned the International Zeolite Association framework, as described in the *Atlas of Zeolite Framework Types*, eds. Ch. Baerlocher, L. B. McCusker and D. H. Olson, Elsevier, 6$^{th}$ revised edition, 2007 and the Database of Zeolite Structures on the International Zeolite Association's website (http://www.iza-online.org).

The term "Periodic Table" refers to the version of IUPAC Periodic Table of the Elements dated Jun. 22, 2007, and the numbering scheme for the Periodic Table Groups is as described in *Chem. Eng. News*, 63(5), 26-27 (1985).

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof. In addition, all number ranges presented herein are inclusive of their upper and lower limit values.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

Reaction Mixture and Crystallization

In preparing SSZ-91, at least one organic compound selective for synthesizing molecular sieves from the ZSM-48 family of zeolites is used as a structure directing agent ("SDA"), also known as a crystallization template. The SDA useful for making SSZ-91 is represented by the following structure (1):

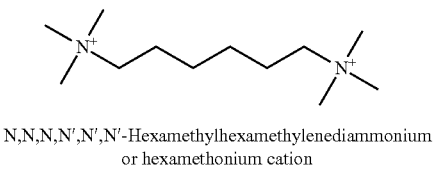

N,N,N,N',N',N'-Hexamethylhexamethylenediammonium or hexamethonium cation

The SDA cation is typically associated with anions which may be any anion that is not detrimental to the formation of the molecular sieve. Representative examples of anions include hydroxide, acetate, sulfate, carboxylate and halogens, for example, fluoride, chloride, bromide and iodide. In one embodiment, the anion is bromide.

In general, SSZ-91 is prepared by:
(a) preparing a reaction mixture containing (1) at least one source of silicon oxide; (2) at least one source of aluminum oxide; (3) at least one source of an element selected from Groups 1 and 2 of the Periodic Table; (4) hydroxide ions; (5) hexamethonium cations; and (6) water; and
(b) maintaining the reaction mixture under crystallization conditions sufficient to form crystals of the molecular sieve.

The composition of the reaction mixture from which the molecular sieve is formed, in terms of mole ratios, is identified in Table 1 below:

TABLE 1

| Components | Broad | Exemplary |
|---|---|---|
| $SiO_2/Al_2O_3$ | 50-220 | 85-180 |
| $M/SiO_2$ | 0.05-1.0 | 0.1-0.8 |
| $Q/SiO_2$ | 0.01-0.2 | 0.02-0.1 |
| $OH/SiO_2$ | 0.05-0.4 | 0.10-0.3 |
| $H_2O/SiO_2$ | 3-100 | 10-50 | wherein,
(1) M is selected from the group consisting of elements from Groups 1 and 2 of the Periodic Table; and
(2) Q is the structure directing agent represented by structure 1 above.

Sources useful herein for silicon include fumed silica, precipitated silica, silica hydrogel, silicic acid, colloidal silica, tetra-alkyl orthosilicates (e.g., tetraethyl orthosilicate), and silica hydroxides.

Sources useful herein for aluminum include aluminates, alumina, and aluminum compounds such as $AlCl_3$, $Al_2(SO_4)_3$, $Al(OH)_3$, kaolin clays, and other zeolites. An example of the source of aluminum oxide is LZ-210 zeolite (a type of Y zeolite).

As described herein above, for each embodiment described herein, the reaction mixture can be formed containing at least one source of an elements selected from Groups 1 and 2 of the Periodic Table (referred to herein as M). In one sub-embodiment, the reaction mixture is formed using a source of an element from Group 1 of the Periodic Table. In another sub-embodiment, the reaction mixture is formed using a source of sodium (Na). Any M-containing compound which is not detrimental to the crystallization process is suitable. Sources for such Groups 1 and 2 elements include oxide, hydroxides, nitrates, sulfates, halides, oxalates, citrates and acetates thereof.

For each embodiment described herein, the molecular sieve reaction mixture can be supplied by more than one source. Also, two or more reaction components can be provided by one source.

The reaction mixture can be prepared either batch wise or continuously. Crystal size, morphology and crystallization time of the molecular sieve described herein can vary with the nature of the reaction mixture and the crystallization conditions.

The reaction mixture is maintained at an elevated temperature until the crystals of the molecular sieve are formed. In general, zeolite hydrothermal crystallization is usually conducted under pressure, and usually in an autoclave so that the reaction mixture is subject to autogenous pressure and optionally stirring, at a temperature between 125° C. and 200° C., for a period of 1 to more than 18 hours.

As noted herein above, SSZ-91 is a substantially phase pure material. As used herein, the term "substantially phase pure material" means the material is completely free of zeolite phases other than those belonging to the ZSM-48 family of zeolites, or are present in quantities that have less than a measureable effect on, or confer less than a material disadvantage to, the selectivity of the material. Two common phases that co-crystalize with SSZ-91 are EUO-type molecular sieves such as EU-1, as well as Magadiite and Kenyaite. These additional phases may be present as separate phases, or may be intergrown with the SSZ-91 phase. As demonstrated in the Examples below, the presence of high amounts of EU-1 in the product is deleterious to the selectivity for hydroisomerization by SSZ-91.

In one embodiment, the SSZ-91 product contains an additional EUO-type molecular sieve phase in an amount of between 0 and 3.5 percent by weight. In one subembodiment, SSZ-91 contains between 0.1 and 2 wt. % EU-1. In another subembodiment, SSZ-91 contains between 0.1 and 1 wt. % EU-1.

It's known that the ratio of powder XRD peak intensities varies linearly as a function of weight fractions for any two phases in a mixture: $(|\alpha|/|\beta|)=(RIR\alpha/RIR\beta)*(x\alpha/x\beta)$, where the RIR (Reference Intensity Ratio) parameters can be found in The International Centre for Diffraction Data's Powder Diffraction File (PDF) database (http://www.icdd.com/products/). The weight percentage of the EUO phase is therefore calculated by measuring the ratio between the peak intensity of the EUO phase and that of the SSZ-91 phase.

The formation of amounts of the EUO phase is suppressed by selecting the optimal hydrogel composition, temperature and crystallization time which minimizes the formation of the EUO phase while maximizing the SSZ-91 product yield. The Examples below provide guidance on how changes in these process variables minimize the formation of EU-1. A zeolite manufacturer with ordinary skill in the art will readily be able to select the process variables necessary to minimize the formation of EU-1, as these variables will depend on the size of the production run, the capabilities of the available equipment, desired target yield and acceptable level of EU-1 material in the product.

During the hydrothermal crystallization step, the molecular sieve crystals can be allowed to nucleate spontaneously from the reaction mixture. The use of crystals of the molecular sieve as seed material can be advantageous in decreasing the time necessary for complete crystallization to occur. In addition, seeding can lead to an increased purity of the product obtained by promoting the nucleation and/or formation of the molecular sieve over any undesired phases. However, it has been found that if seeding is employed, the seeds must be very phase-pure SSZ-91 to avoid the formation of a large amount of a EUO phase. When used as seeds, seed crystals are added in an amount between 0.5% and 5% of the weight of the silicon source used in the reaction mixture.

The formation of Magadiite and Kenyaite is minimized by optimizing the hexamethonium bromide/$SiO_2$ ratio, controlling the hydroxide concentration, and minimizing the concentration of sodium as Magadiite and Kenyaite are layered sodium silicate compositions. The Examples below provide guidance on how changes in gel conditions minimize the formation of EU-1.

Once the molecular sieve crystals have formed, the solid product is separated from the reaction mixture by standard mechanical separation techniques such as filtration. The crystals are water-washed and then dried to obtain the as-synthesized molecular sieve crystals. The drying step can be performed at atmospheric pressure or under vacuum.

Post-Crystallization Treatment

The molecular sieve can be used as-synthesized, but typically will be thermally treated (calcined). The term "as-synthesized" refers to the molecular sieve in its form after crystallization, prior to removal of the SDA cation. The SDA can be removed by thermal treatment (e.g., calcination), preferably in an oxidative atmosphere (e.g., air, gas with an oxygen partial pressure of greater than 0 kPa) at a temperature readily determinable by one skilled in the art sufficient to remove the SDA from the molecular sieve. The SDA can also be removed by ozonation and photolysis techniques (e.g., exposing the SDA-containing molecular sieve product to light or electromagnetic radiation that has a wavelength shorter than visible light under conditions sufficient to selectively remove the organic compound from the molecular sieve) as described in U.S. Pat. No. 6,960,327.

The molecular sieve can subsequently be calcined in steam, air or inert gas at temperatures ranging from 200° C. to 800° C. for periods of time ranging from 1 to 48 hours, or more. Usually, it is desirable to remove the extra-framework cation (e.g., $Na^+$) by ion exchange and replace it with hydrogen, ammonium, or any desired metal-ion.

Where the molecular sieve formed is an intermediate molecular sieve, the target molecular sieve can be achieved using post-synthesis techniques such as heteroatom lattice substitution techniques. The target molecular sieve (e.g., silicate SSZ-91) can also be achieved by removing heteroatoms from the lattice by known techniques such as acid leaching.

The molecular sieve made from the process disclosed herein can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the molecular sieve can be extruded before drying, or, dried or partially dried and then extruded.

The molecular sieve can be composited with other materials resistant to the temperatures and other conditions employed in organic conversion processes. Such matrix materials include active and inactive materials and synthetic or naturally occurring molecular sieves as well as inorganic materials such as clays, silica and metal oxides. Examples of such materials and the manner in which they can be used are disclosed in U.S. Pat. Nos. 4,910,006 and 5,316,753.

The extrudate or particle may then be further loaded using a technique such as impregnation or ion-exchange, with one or more active metals selected from the group consisting of metals from Groups 8 to 10 of the Periodic Table, to enhance the hydrogenation function. It may be desirable to co-impregnate a modifying metal and one or more Group 8 to 10 metals at once, as disclosed in U.S. Pat. No. 4,094,821. In one embodiment, the at least one active metal is selected from the group consisting of nickel, platinum, palladium, and combinations thereof. After metal loading, the metal loaded extrudate or particle can be calcined in air or inert gas at temperatures from 200° C. to 500° C. In one embodiment, the metal loaded extrudate is calcined in air or inert gas at temperatures from 390° C. to 482° C.

SSZ-91 is useful for a variety of hydrocarbon conversion reactions such as hydrocracking, dewaxing, olefin isomerization, alkylation and isomerization of aromatic compounds and the like. SSZ-91 is also useful as an adsorbent for general separation purposes.

Characterization of the Molecular Sieve

Molecular sieves made by the process disclosed herein have $SiO_2/Al_2O_3$ mole ratio (SAR) of 40 to 200. The SAR is determined by inductively coupled plasma (ICP) elemental analysis. In one subembodiment, SSZ-91 has a SAR of between 70 and 160. In another subembodiment, SSZ-91 has a SAR of between 80 and 140.

SSZ-91 materials are composed of at least 70% polytype 6 of the total ZSM-48-type material present in the product, as determined by DIFFaX simulation and as described by Lobo and Koningsveld in J. Am. Chem. Soc. 2012, 124, 13222-13230, where the disorder was tuned by three distinct fault probabilities. It should be noted the phrase "at least X %" includes the case where there are no other ZSM-48 polytypes present in the structure, i.e., the material is 100% polytype 6. The structure of polytype 6 is as described by Lobo and Koningsveld. (See, J. Am. Chem. Soc. 2002, 124, 13222-13230). In one embodiment, the SSZ-91 material is composed of at least 80% polytype 6 of the total ZSM-48-type material present in the product. In another embodiment, the SSZ-91 material is composed of at least 90% polytype 6 of the total ZSM-48-type material present in the product. The polytype 6 structure has been given the framework code *MRE by the Structure Commission of the International Zeolite Association.

Molecular sieve SSZ-91 has a morphology characterized as polycrystalline aggregates having a diameter of between about 100 nm and 1.5 µm, each of the aggregates comprising a collection of crystallites collectively having an average aspect ratio of between 1 and 8. As used herein, the term diameter refers to the shortest length on the short end of each crystallite examined. SSZ-91 exhibits a lower degree of hydrocracking than those ZSM-48 materials having a higher aspect ratio. In one subembodiment, the average aspect ratio is between 1 and 5. In another subembodiment, the average aspect ratio is between 1 and 4. In yet another subembodiment, the average aspect ratio is between 1 and 3.

Molecular sieves synthesized by the process disclosed herein can be characterized by their XRD pattern. The powder XRD lines of Table 2 are representative of as-synthesized SSZ-91 made in accordance with the methods described herein. Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation and from variations in the Si/Al mole ratio from sample to sample. Calcination can also cause minor shifts in the XRD pattern. Notwithstanding these minor perturbations, the basic crystal lattice structure remains unchanged.

TABLE 2

Characteristic Peaks for As-Synthesized SSZ-91

| 2-Theta[a] | d-spacing (nm) | Relative Intensity[b] |
|---|---|---|
| 7.55 | 1.170 | W |
| 8.71 | 1.015 | W |
| 12.49 | 0.708 | W |
| 15.12 | 0.586 | W |
| 21.18 | 0.419 | VS |
| 22.82 | 0.390 | VS |
| 24.62 | 0.361 | W |
| 26.39 | 0.337 | W |
| 29.03 | 0.307 | W |
| 31.33 | 0.285 | W |

[a]±0.20
[b]The powder XRD patterns provided are based on a relative intensity scale in which the strongest line in the X-ray pattern is assigned a value of 100: W = weak (>0 to ≤20); M = medium (>20 to ≤40); S = strong (>40 to ≤60); VS = very strong (>60 to ≤100).

The X-ray diffraction pattern lines of Table 3 are representative of calcined SSZ-91 made in accordance with the methods described herein.

TABLE 3

Characteristic Peaks for Calcined SSZ-91

| 2-Theta[a] | d-spacing (nm) | Relative Intensity[b] |
|---|---|---|
| 7.67 | 1.152 | M |
| 8.81 | 1.003 | W |
| 12.61 | 0.701 | W |
| 15.30 | 0.579 | W |
| 21.25 | 0.418 | VS |
| 23.02 | 0.386 | VS |
| 24.91 | 0.357 | W |
| 26.63 | 0.334 | W |
| 29.20 | 0.306 | W |
| 31.51 | 0.284 | W |

[a]±0.20
[b]The powder XRD patterns provided are based on a relative intensity scale in which the strongest line in the X-ray pattern is assigned a value of 100: W = weak (>0 to ≤20); M = medium (>20 to ≤40); S = strong (>40 to ≤60); VS = very strong (>60 to ≤100).

The powder X-ray diffraction patterns presented herein were collected by standard techniques. The radiation was CuK$_\alpha$ radiation. The peak heights and the positions, as a function of 2θ where θ is the Bragg angle, were read from the relative intensities of the peaks (adjusting for background), and d, the interplanar spacing corresponding to the recorded lines, can be calculated.

EXAMPLES

The following illustrative examples are intended to be non-limiting.

Summary of the Examples

The Examples below demonstrate that a ZSM-48 material lacking any one of the three uniquely combined characteristics of SSZ-91 (low aspect ratio, low EU-1 content, high polytype 6 composition) will exhibit poor catalytic performance. Table 4 below summarizes the hydroprocessing performance for various Examples outlined below. Only Example 8 (SSZ-91) exhibited superior performance, namely superior selectivity and low gas make as compared to the other three Examples. The remaining materials tested in the other three Examples exhibited poor performance because each lacked at least one of the three uniquely combined characteristics that define SSZ-91.

TABLE 4

| Examples | % Polytype 6 | % EU-1 | Aspect Ratio | Isomerization Selectivity at 96% (n-C$_{16}$ Conversion) | C$_4^-$ Cracking |
|---|---|---|---|---|---|
| Comparative Example 1 | 80 | <1 | 7-12 | 78% | 2.8% |
| Example 8 | >90 | 3.20 | 1-4 | 87% | 1.5% |
| Example 11 | >90 | 6.82 | 2-6 | 82% | 2.6% |
| Example 13 | >90 | 3.16 | 9-15 | 78% | 2.2% |

Comparative Example 1

Synthesis of ZSM-48

The product in this Example was prepared according to the teachings of U.S. Pat. No. 5,075,269 to Thomas F. Degnan and Ernest W. Valyocsik (Mobil Oil Corp.) issued Dec. 24, 1991, using available reagents.

Into a 1-gallon autoclave liner were added 76.51 g of NaOH (50%), 846 g of de-ionized water, 124.51 g of HI-SIL 233 silica (PPG Industries), and 63 g of hexamethonium bromide ("HMB," Sigma Aldrich). After all the solids had dissolved, 396 g of aluminum stock solution prepared by dissolving 4.35 g $Al_2(SO_4)_3.18H_2O$ and 63 g conc. $H_2SO_4$ in 733.52 g de-ionized water, was added. Finally, 0.45 g of SSZ-91 seed crystals from Example 7 was added. The mixture was stirred until homogeneous. The composition of the aluminosilicate gel produced had the following mole ratios:

TABLE 5

| | |
|---|---|
| $SiO_2/Al_2O_3$ | 220 |
| $H_2O/SiO_2$ | 39.9 |
| $OH^-/SiO_2$ | 0.21 |
| $Na^+/SiO_2$ | 0.56 |

TABLE 5-continued

| | |
|---|---|
| $HMB/SiO_2$ | 0.10 |
| Seed | 0.38% |

Figure 2:
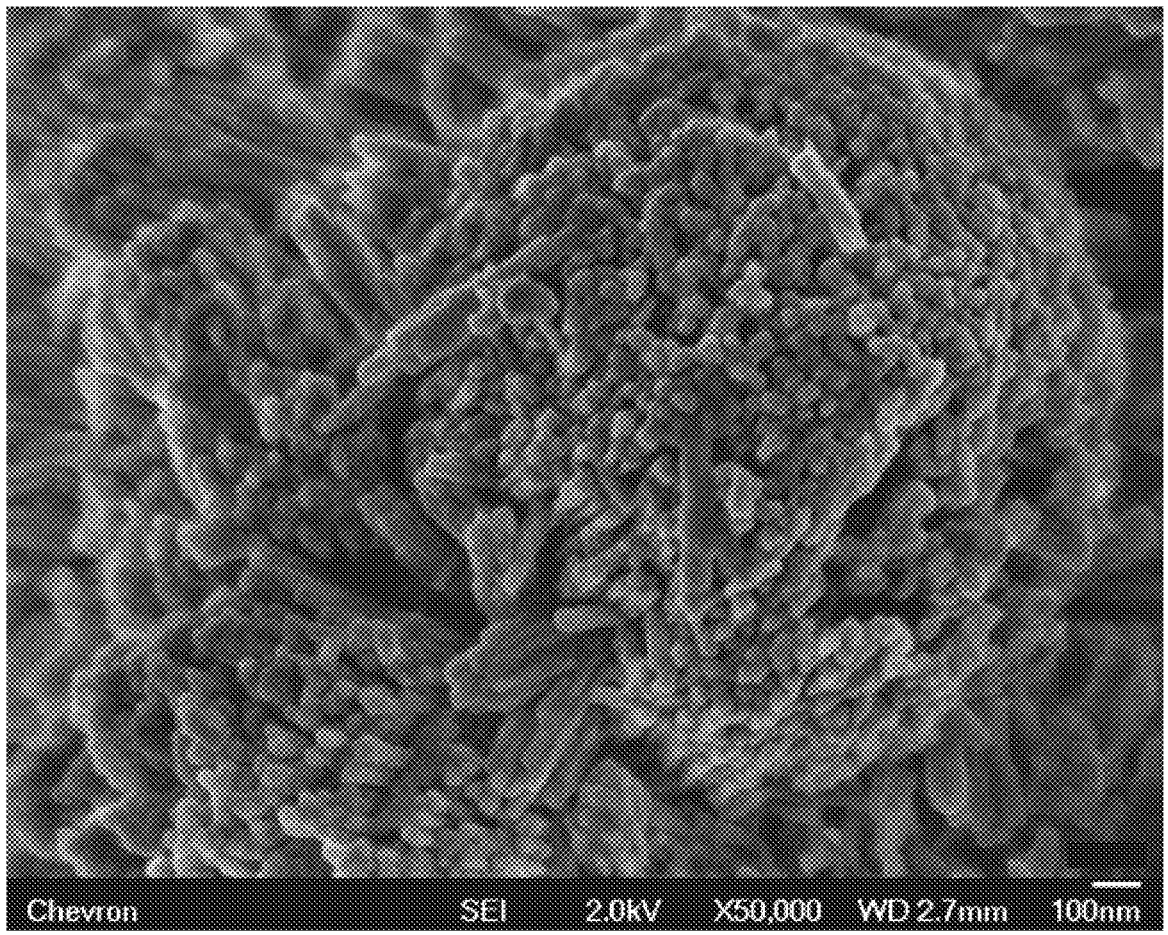
FIG. 2 is a scanning electron micrograph of as-synthesized molecular sieve prepared in Comparative Example 1.

The liner was transferred to a 1-gallon autoclave, which was heated to 160° C. over a period of 8 hours, and stirred at a rate of 150 rpm at autogenous pressure. After 80 hours, the product was filtered, washed with de-ionized water and dried. The resulting solids were determined by XRD to be a ZSM-48 material (FIG. 1). The XRD indicated there was an immeasurable amount of EU-1 in the product (likely less than 1% EU-1). The SEM shows agglomerated long needles of ZSM-48 crystals (FIG. 2), with an aspect ratio of 7-12.

Comparative Examples 2 and 3

Figure 3:
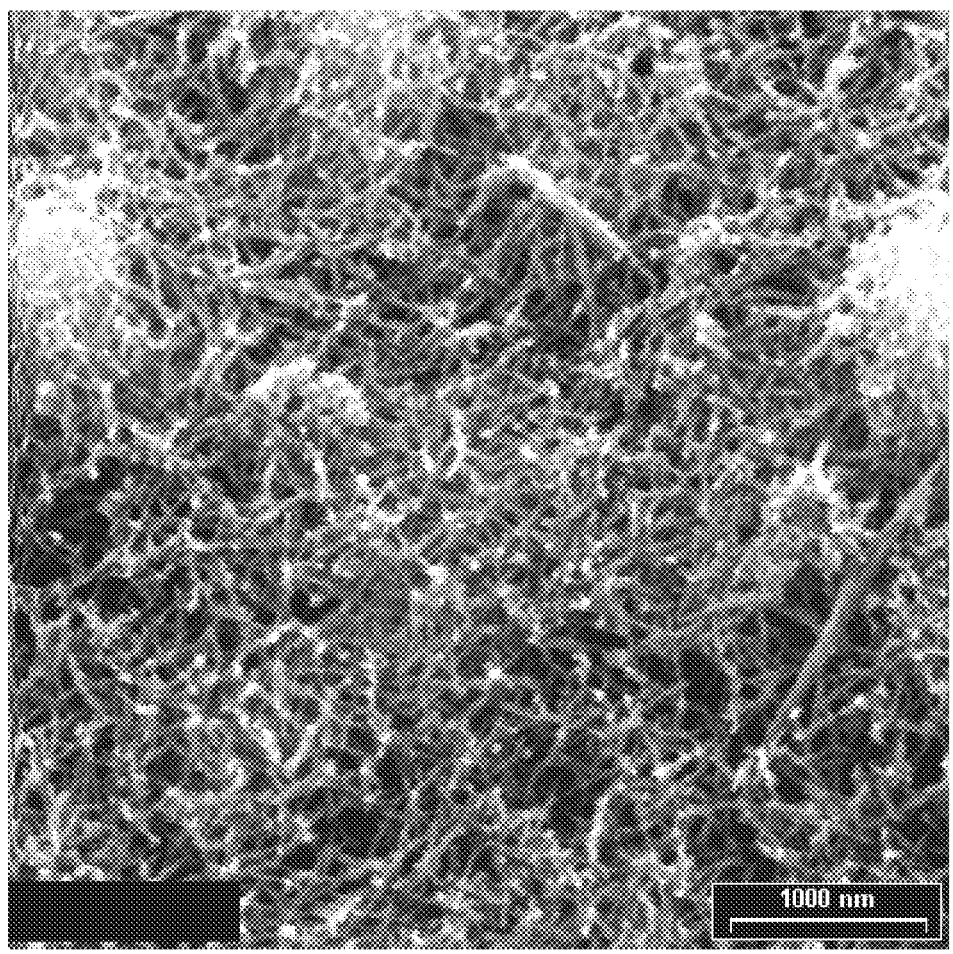
FIG. 3 is a scanning electron micrograph of as-synthesized molecular sieve prepared in Comparative Example 2.
Figure 4:
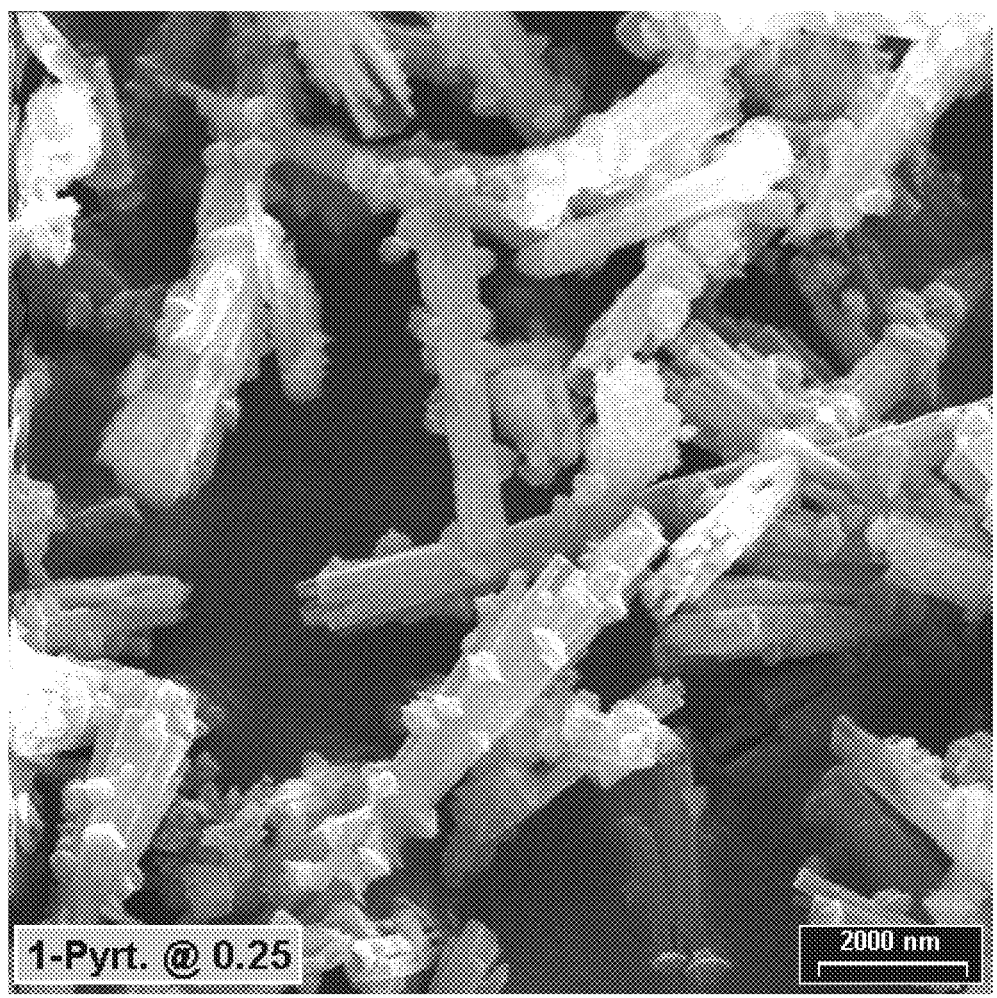
FIG. 4 is a scanning electron micrograph of as-synthesized molecular sieve prepared in Comparative Example 3.

As noted above, the Lobo and Koningsveld paper describes their analysis of three ZSM-48 samples provided by Dr. Alexander Kuperman of Chevron Corporation. Each of the three samples, Samples A, B and C, respectively, were prepared using three different structure directing agents. The Lobo and Koningsveld paper describes Sample A as being polytype 6, and Sample B as being a faulted polytype 6. The paper further describes the morphology of Sample A (FIG. 3) of consisting of thin needle-like crystals having a diameter of ~20 nm and a length of ~0.5 μm. The morphology of Sample B (FIG. 4) consisted of long, narrow crystals having a diameter of ~30 nm and a length of 4-8 μm. Even though Dr. Kuperman's materials were reported as having a high concentration of polytype 6, the samples are characterized as having aspect ratios (length/diameter) of 25 for Sample A, and an aspect ratio ranging between 133 and 266 for Sample B.

Examples 4-11

Synthesis of SSZ-91 with Varying EU-1 Concentrations in the Product

Each of Examples 4 through 11 were prepared by adding NaOH (50%), de-ionized water, HI-SIL 233 silica (PPG Industries), hexamethonium bromide (Sigma Aldrich) to an autoclave liner. After all the solids had dissolved, an aluminum stock solution prepared by dissolving 4.18 g $Al_2(SO_4)_3.18H_2O$ and 45.58 g conc. $H_2SO_4$ in 540.6 g de-ionized water, was added. The mixture was stirred until homogeneous. The mole ratios for the aluminosilicate gels and heating periods are listed in Table 6 below.

TABLE 6

| | Example No. | | | | | | | |
|---|---|---|---|---|---|---|---|---|
| | 4 | 5 | 6 | 7 | 8 | 9 | 10 | 11 |
| $SiO_2/Al_2O_3$ | 218.6 | 113.6 | 177.8 | 180 | 177.7 | 177.7 | 177.7 | 170.0 |
| $H_2O/SiO_2$ | 40.0 | 23.0 | 40.3 | 40.0 | 40.3 | 40.3 | 40.3 | 40 |
| $OH^-/SiO_2$ | 0.21 | 0.17 | 0.27 | 0.28 | 0.27 | 0.27 | 0.27 | 0.27 |
| $Na^+/SiO_2$ | 0.56 | 0.17 | 0.21 | 0.71 | 0.71 | 0.71 | 0.71 | 0.46 |
| $HMB/SiO_2$ | 0.10 | 0.02 | 0.10 | 0.10 | 0.10 | 0.10 | 0.10 | 0.10 |
| Crystallization Period (hrs) | 38 | 48 | 30 | 34 | 30 | 30 | 30 | 30 |

The liner was transferred to an autoclave, which was heated to 160° C. over a period of 8 hours, and stirred at a rate of 150 rpm at autogenous pressure. After the crystallization period, the product was filtered, washed with de-ionized water and dried. The resulting solids were analyzed by XRD to determine the product and the level of EU-1 in the product. The bulk $SiO_2/Al_2O_3$ mole ratio and EU-1 content are listed in Table 7 below.

TABLE 7

| | Example No. | | | | | | | |
|---|---|---|---|---|---|---|---|---|
| | 4 | 5 | 6 | 7 | 8 | 9 | 10 | 11 |
| Percent EU-1 | 0.25 | 0.30 | 2.09 | 3.13 | 3.20 | 3.22 | 3.56 | 6.82 |
| Bulk $SiO_2/Al_2O_3$ mole ratio | 155 | 88 | 101 | 140 | 130 | 125 | 123 | 118 |

Figure 5:
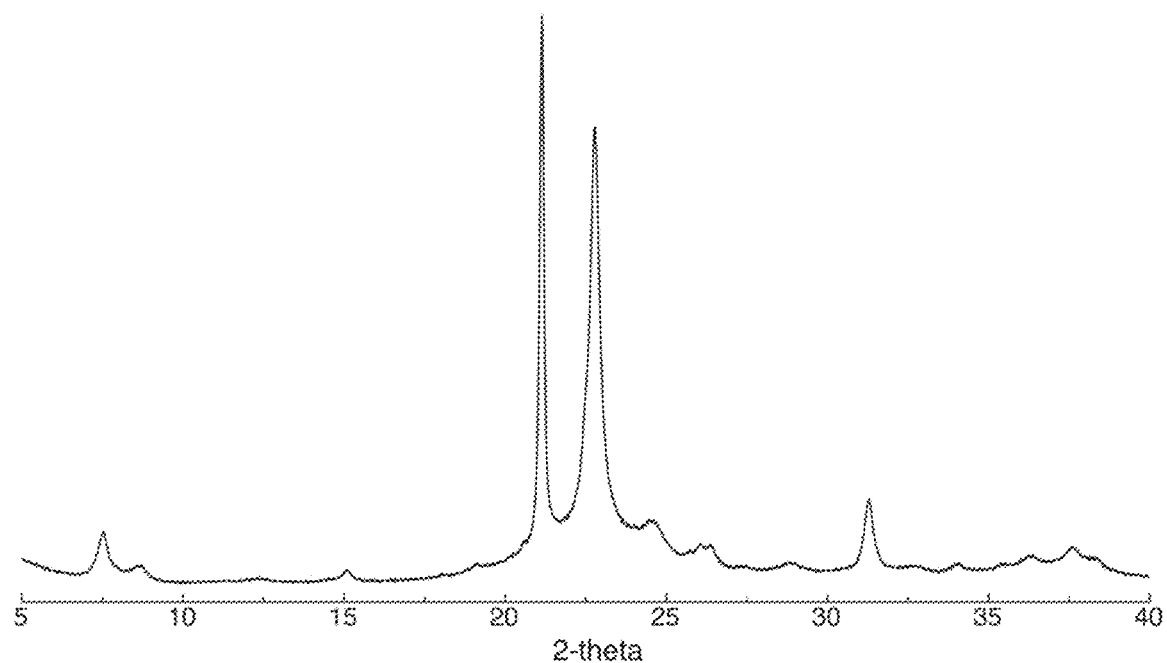
FIG. 5 is a powder XRD pattern of as-synthesized molecular sieve SSZ-91 prepared in Example 7.

The products from Examples 1 and 4-11 were analyzed by XRD and SEM. The XRD pattern for Example 7 is shown in FIG. 5, and is illustrative of the XRD patterns collected for the remaining Examples 4-11.

Figure 6:
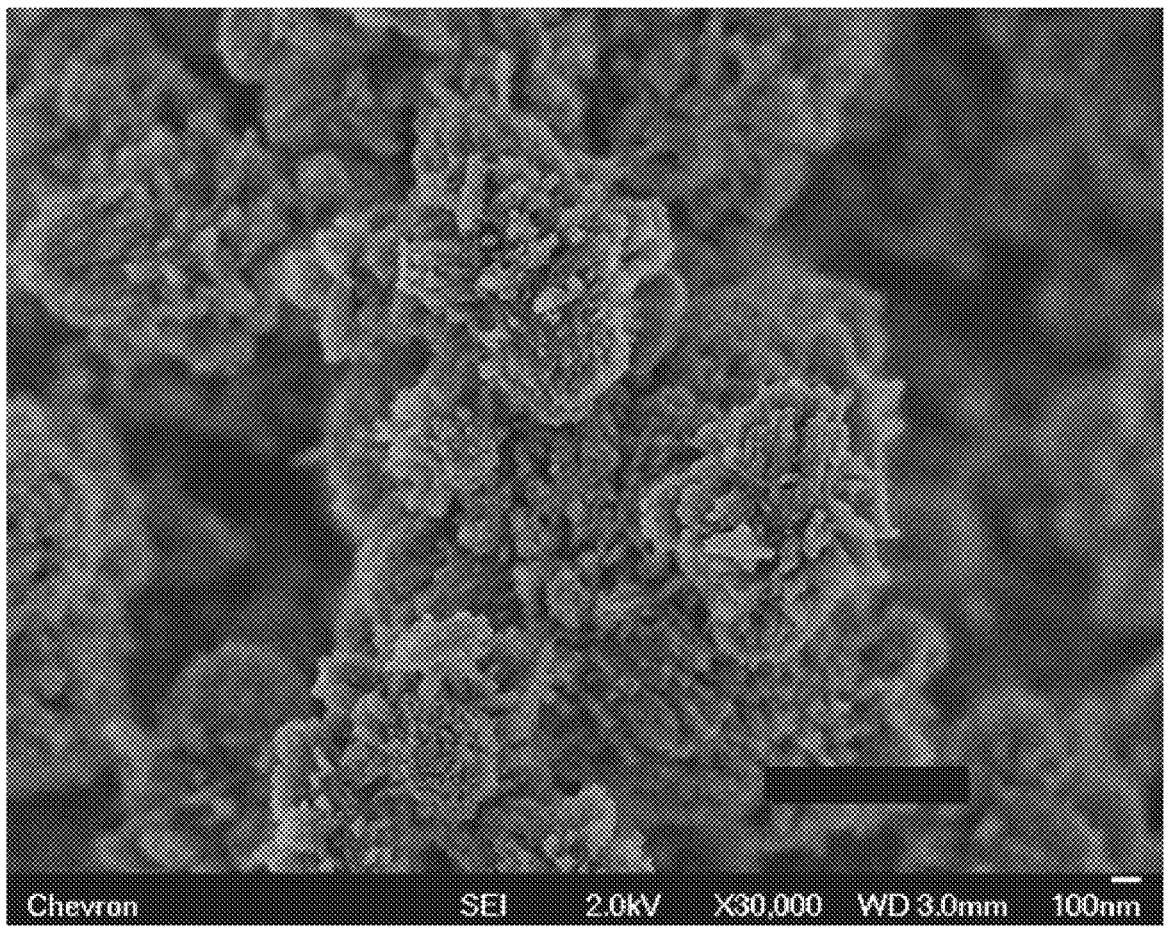
FIG. 6 is a scanning electron micrograph of as-synthesized molecular sieve SSZ-91 prepared in Example 7.
Figure 7:
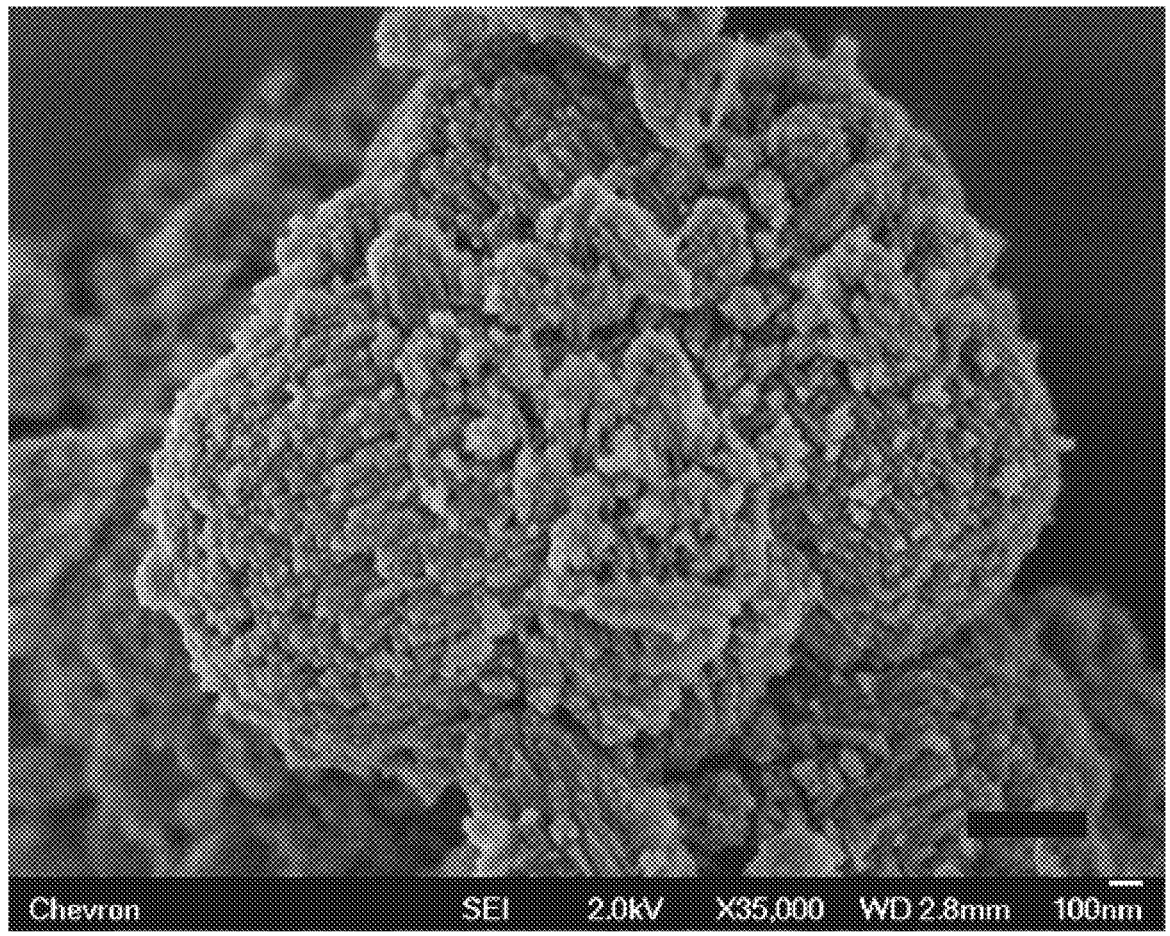
FIG. 7 is a scanning electron micrograph of as-synthesized molecular sieve prepared in Example 8.

The SEM image for Examples 7 and 8 are shown in FIGS. 6 and 7, respectively, and are illustrative of the SEM images for the remaining Examples 4-11. FIGS. 6 and 7 show the SSZ-91 material consists of polycrystalline aggregates, each of the aggregates composed of crystallites, wherein each crystallite has characteristic average aspect ratio of less than 8. In contrast, the ZSM-48 materials of Comparative Examples 1-3 (FIGS. 2-4) contained long needles and fibrous morphologies, the presence of which have consistently showed poor catalytic performance.

Calcination and Ion-Exchange of Molecular Sieves

The as-synthesized products from Comparative Example 1 and Examples 4-11 were converted into the sodium form under an atmosphere of dry air at a heating rate of 1° C./min. to 120° C. and held for 120 min followed by a second ramp of 1° C./min. to 540° C. and held at this temperature for 180 min and lastly a third ramp of 1° C./min. to 595° C. and held at this temperature for 180 min. Finally, the sample was cooled down to 120° C. or below. Each of these calcined samples was then exchanged into the ammonium form as follows. An amount of ammonium nitrate equal to the mass of the sample to be exchanged was fully dissolved in an amount of deionized water ten times the mass of the sample. The sample was then added to the ammonium nitrate solution and the suspension was sealed in a flask and heated in an oven at 95° C. overnight. The flask was removed from the oven, and the sample was recovered immediately by filtration. This ammonium exchange procedure was repeated on the recovered sample, washed with copious amount of deionized water to a conductivity of less than 50 μS/cm and finally dried in an oven at 95° C. for three hours.

Hydroprocessing Tests

Palladium ion-exchange was carried out on the ammonium-exchanged samples from Examples 1 and 4-11 using tetraamminepalladium(II) nitrate (0.5 wt % Pd). After ion-exchange, the samples were dried at 95° C. and then calcined in air at 482° C. for 3 hours to convert the tetraamminepalladium(II) nitrate to palladium oxide.

0.5 g of each of the palladium exchanged samples from Example 11 was loaded in the center of a 23 inch-long by 0.25 inch outside diameter stainless steel reactor tube with alundum loaded upstream of the catalyst for pre-heating the feed (total pressure of 1200 psig; down-flow hydrogen rate of 160 mL/min (when measured at 1 atmosphere pressure and 25° C.); down-flow liquid feed rate of 1 mL/hour. All materials were first reduced in flowing hydrogen at about 315° C. for 1 hour. Products were analyzed by on-line capillary gas chromatography (GC) once every thirty minutes. Raw data from the GC was collected by an automated data collection/processing system and hydrocarbon conversions were calculated from the raw data.

The catalyst was tested at about 260° C. initially to determine the temperature range for the next set of measurements. The overall temperature range will provide a wide range of hexadecane conversion with the maximum conversion just below and greater than 96%. At least five on-line GC injections were collected at each temperature. Conversion was defined as the amount of hexadecane reacted to produce other products (including iso-$nC_{16}$ isomers). Yields were expressed as weight percent of products other than n-$C_{16}$ and included iso-$C_{16}$ as a yield product. The results are included in Table 8.

TABLE 8

| Examples | Percent EU-1 | Isomerization Selectivity at 96% (n-$C_{16}$ Conversion) | Temperature (° F.) | $C_4^-$ Cracking |
|---|---|---|---|---|
| Example 4 | 0.25 | 88% | 606 | 1.3% |
| Example 5 | 0.30 | 88% | 565 | 1.2% |
| Example 6 | 2.09 | 85% | 584 | 1.7% |
| Example 7 | 3.13 | 85% | 598 | 1.7% |
| Example 8 | 3.20 | 87% | 601 | 1.5% |
| Example 9 | 3.22 | 87% | 597 | 1.6% |
| Example 10 | 3.56 | 86% | 600 | 1.6% |
| Example 11 | 6.82 | 82% | 593 | 2.6% |

The desirable isomerization selectivity at 96% conversion for the preferred materials of this invention is at least 85%. A good balance between isomerization selectivity and temperature at 96% conversion is critical for this invention. The desirable temperature at 96% conversion is less than 605° F. The lower the temperature at 96% conversion the more desirable is the catalyst whilst still maintaining isomerization selectivity of at least 85%. The best catalytic performance is dependent on the synergy between isomerization selectivity and temperature at 96% conversion. A large amount of impurity results in undesirable catalytic cracking with concomitant high gas make reflected in Table 8 by increased level of $C_4^-$ cracking. The desirable $C_4^-$ cracking for the materials of this invention is below 2.0%. Note the selectivity begins to decrease at 6.82% EU-1, because increasing concentrations of EU-1 promotes catalytic cracking.

Polytype Distribution

Figure 8:
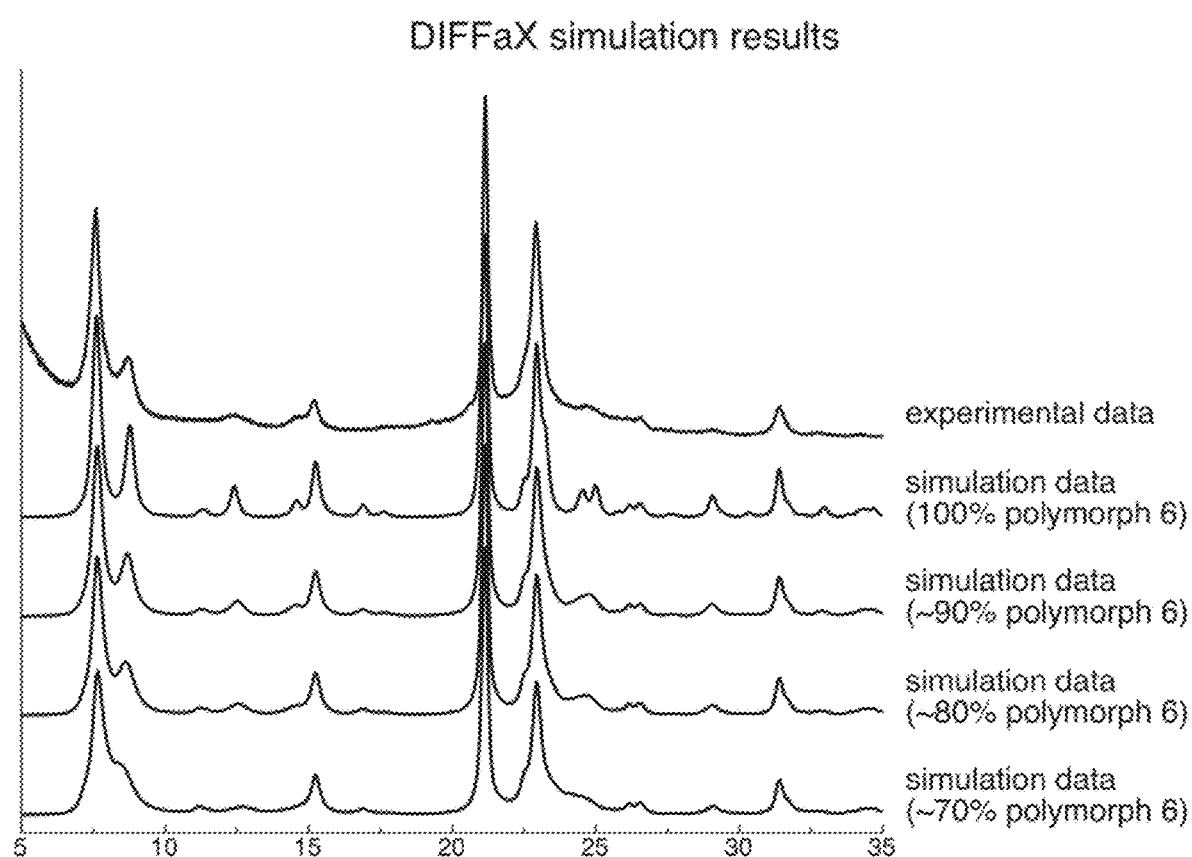
FIG. 8 is a plot of several DIFFaX-generated simulated XRD patterns and a powder XRD pattern of the as-synthesized molecular sieve SSZ-91 prepared in Example 8.
Figure 9:
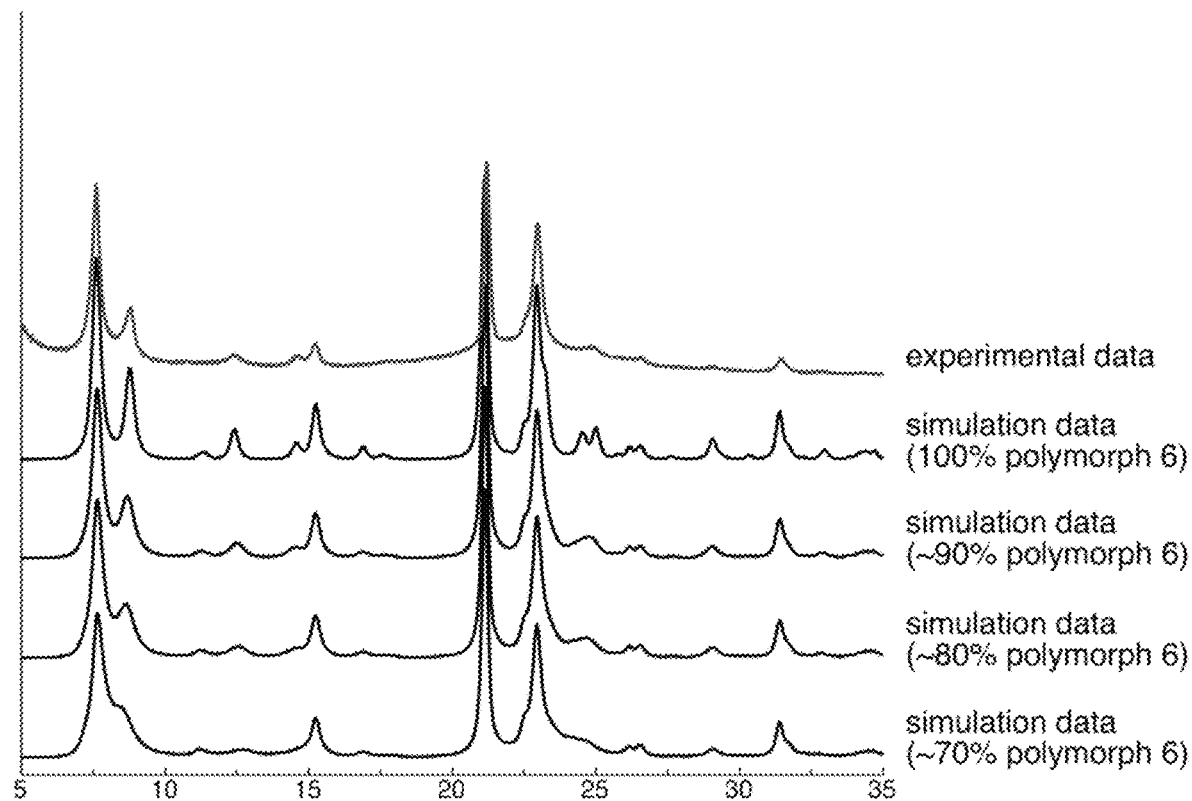
FIG. 9 is a plot of several DIFFaX-generated simulated XRD patterns and a powder XRD pattern of the as-synthesized molecular sieve prepared in Example 11.

Using DIFFaX, simulated XRD patterns for ZSM-48 materials having between 70 and 100% polytype 6 were generated and compared to the XRD pattern collected for the molecular sieve product from Examples 8 and 11. The simulated and product XRD patterns are presented in FIGS. 8 and 9 herein, respectively. A comparison of the product XRD pattern to the simulated patterns indicates the product synthesized in Examples 8 and 11 contained greater than 90% polytype 6.

Figure 10:
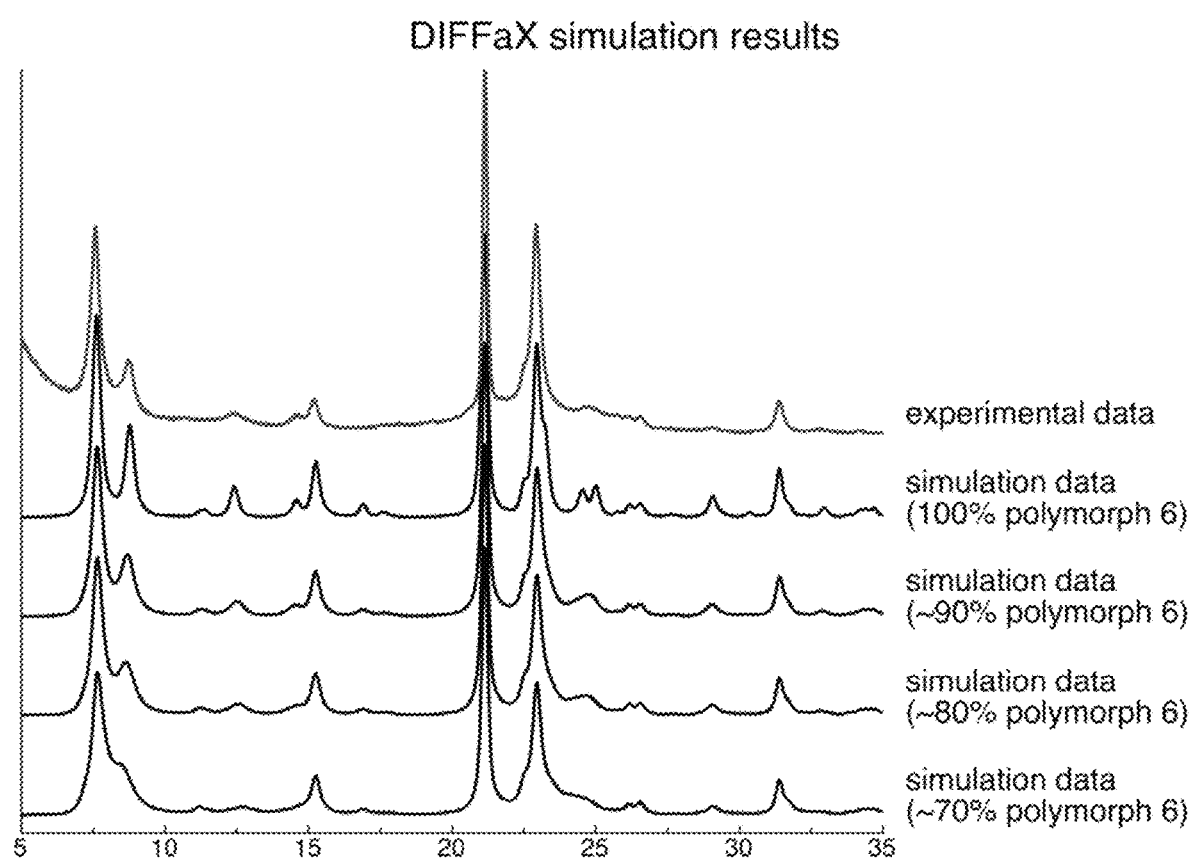
FIG. 10 is a plot of several DIFFaX-generated simulated XRD patterns and a powder XRD pattern of the as-synthesized molecular sieve prepared in Comparative Example 1.

Using DIFFaX, simulated XRD patterns for ZSM-48 materials having between 70 and 100% polytype 6 were generated and compared to the XRD pattern collected for the molecular sieve product from Comparative Example 1. The simulated and product XRD patterns are presented in FIG. 10 herein. A comparison of the product XRD pattern to the simulated patterns indicates the product synthesized in Comparative Example 1 contained 80% polytype 6.

The material synthesized in Comparative Example 1 was subjected to the hexadecane hydroprocessing test as outlined for Examples 4-11 above. The material from Comparative Example 1 exhibited an isomerization selectivity of 78% at 96% conversion at a temperature of 614° F. As indicated in Table 9 below, the $C_4^-$ cracking was 2.8%. The isomerization selectivity at 96% conversion for the Comparative Example 1 material, having a polytype 6 content of only 80%, was inferior to those described in Examples 4 through 10, as shown in Table 7 above, even though the material of Comparative Example 1 contained an immeasurable (<1%) amount of EU-1. This indicates that although the material of Comparative Example 1 and Example 11 exhibited two of the three characteristics of SSZ-91 (low aspect ratio, low EU-1 content, high polytype 6 content), the lack of the third characteristic contributed to the material's poor catalytic performance.

TABLE 9

| Examples | % Polytype 6 | % EU-1 | Aspect Ratio | Isomerization Selectivity at 96% (n-$C_{16}$ Conversion) | $C_4^-$ Cracking |
|---|---|---|---|---|---|
| Comparative Example 1 | 80 | <1 | 7-12 | 78% | 2.8% |
| Example 8 | >90 | 3.20 | 1-4 | 87% | 1.5% |
| Example 11 | >90 | 6.82 | 2-6 | 82% | 2.6% |

Example 12-13

Synthesis of SSZ-91 with Alternate Silica Source

The material of Example 12 was prepared by adding NaOH (50%), de-ionized water, CAB-O-SIL M-5 silica (Cabot Corporation) and hexamethonium bromide (HMB) to an autoclave liner. After all the solids had dissolved, anhydrous, Riedel de Haen sodium aluminate was added. Lastly, slurry of SSZ-91 similar to the slurry from Example 4 was added. The mixture was stirred until homogeneous. The composition of the aluminosilicate gel produced possessed the following mole ratios:

TABLE 10

| | |
|---|---|
| $SiO_2/Al_2O_3$ | 113.6 |
| $H_2O/SiO_2$ | 23.0 |
| $OH^-/SiO_2$ | 0.17 |
| $Na^+/SiO_2$ | 0.17 |
| $HMB/SiO_2$ | 0.02 |
| Seed | 2.92% |

The liner was transferred to an autoclave, which was heated to 160° C. over a period of 8 hours, and stirred at a rate of 150 rpm at autogenous pressure. After 48 hours, the product was filtered, washed with de-ionized water and dried. The resulting solids were determined by XRD to be SSZ-91 and contained a 0.30 wt % of EUO. The bulk $SiO_2/Al_2O_3$ mole ratio was found to be about 102.

The material of Example 13 was prepared by adding NaOH (50%), de-ionized water, commercially available NALCO 2327 colloidal silica (40.3% $SiO_2$) and hexamethonium bromide to an autoclave liner. After all the solids had dissolved, $Al_2(SO_4)_3 \cdot 18H_2O$ previously dissolved in some of the water was added. The mixture was stirred until homogeneous. The composition of the aluminosilicate gel produced possessed the following mole ratios:

TABLE 11

| | |
|---|---|
| $SiO_2/Al_2O_3$ | 177.7 |
| $H_2O/SiO_2$ | 20.0 |
| $OH^-/SiO_2$ | 0.13 |
| $Na^+/SiO_2$ | 0.17 |
| $HMB/SiO_2$ | 0.05 |

Figure 11:
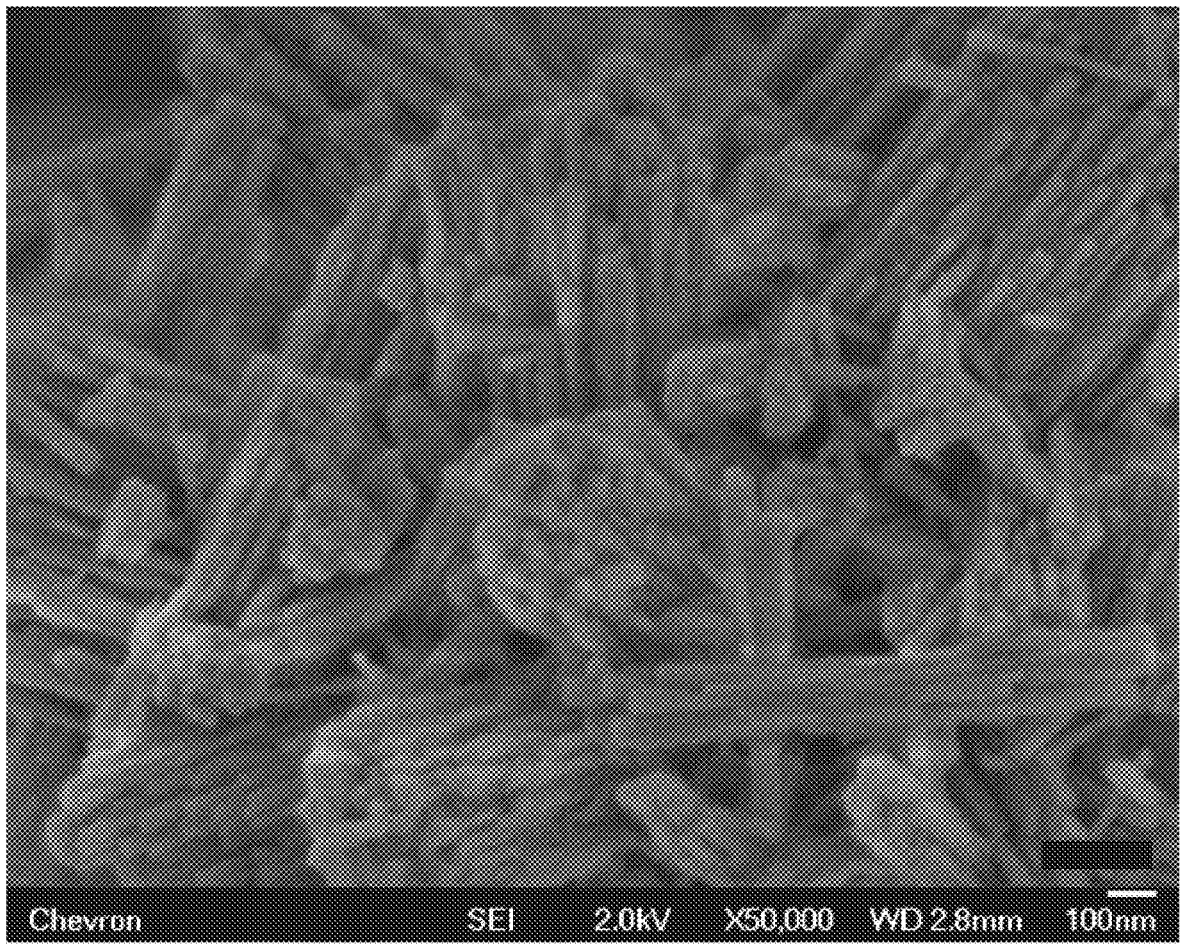
FIG. 11 is a scanning electron micrograph of as-synthesized molecular sieve prepared in Example 13.

The liner was transferred to an autoclave, which was heated to 160° C. over a period of 8 hours, and stirred at a rate of 150 rpm at autogenous pressure. After 35 hours, the product was filtered, washed with de-ionized water and dried. The resulting solids were determined by XRD to be SSZ-91 and contained a 3.16 wt % of EU-1. The bulk $SiO_2/Al_2O_3$ mole ratio was found to be about 155. The material of Example 13 was analyzed by scanning electron microscopy, and an SEM image from that analysis is shown in FIG. 11.

Hydroprocessing Tests

For the SSZ-91 materials synthesized in Examples 12 and 13, palladium loading and catalytic tests were carried out as described with respect to the Examples above. The results of the catalytic tests are shown below in Table 12. These two examples prepared by varying the raw materials used show the versatility of SSZ-91 preparations. Example 12 showed another good example of desirable isomerization selectivity, 88% at significantly lower temperature at 96%. Example 13, although phase pure, but showed inferior catalytic performance, a result of the crystal habit with poor aspect ratio of the crystals.

TABLE 12

| Example | Percent EUO | Aspect Ratio | % Polytype 6 | Isomerization Selectivity at 96% (n-$C_{16}$ Conversion) | Temperature (° F.) | $C_4$-minus Cracking |
|---|---|---|---|---|---|---|
| Example 12 | 0.30 | 1-3 | >90 | 88% | 559 | 1.3% |
| Example 13 | 3.16 | >10 | >90 | 78% | 587 | 2.2% |

Figure 12:
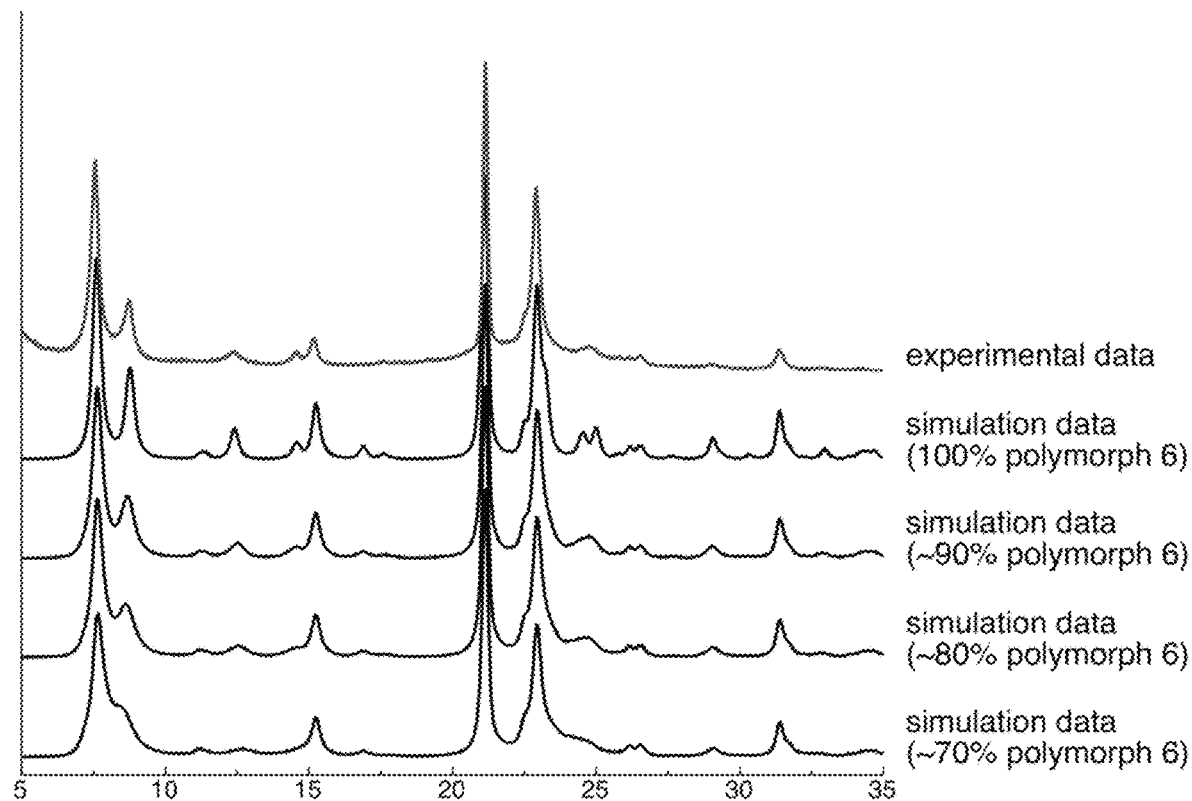
FIG. 12 is a plot of several DIFFaX-generated simulated XRD patterns and a powder XRD pattern of the as-synthesized molecular sieve prepared in Example 13.

Using DIFFaX, simulated XRD patterns for ZSM-48 materials having between 70 and 100% polytype 6 were generated and compared to the XRD pattern collected for the molecular sieve product from Example 13. The simulated and product XRD patterns are presented in FIG. 12 herein. An SEM image from that analysis is shown in FIG. 11 A comparison of the product XRD pattern to the simulated patterns indicates the product synthesized in Comparative Example 1 contains greater than 90% polytype 6. This indicates that although the material of Example 13 had the requisite low EU-1 content and desired polytype distribution, the high aspect ratio contributed to the material's poor catalytic performance. Example 13 again demonstrates that the lack of any one of the three characteristics of SSZ-91 (low aspect ratio, low EU-1 content, high polytype 6 content) contributes to the material's poor catalytic performance.

What is claimed is:

1. A catalyst, suitable for use in hydrocarbon hydrocracking, dewaxing, and olefin isomerization reactions, and in the alkylation and isomerization of aromatic compounds, the catalyst comprising a molecular sieve belonging to the ZSM-48 family of zeolites, wherein the molecular sieve comprises:
   at least 70% polytype 6 of the total ZSM-48-type material present in the product, and
   an additional EUO-type molecular sieve phase in an amount of between 0 and 3.5 percent by weight of the total product; and
   wherein the molecular sieve has a morphology characterized as polycrystalline aggregates comprising crystallites collectively having an average aspect ratio of between 1 and 8, and wherein, the catalyst comprises one or more modifying metals selected from Groups 8 to 10 metals of the Periodic Table, and is composited with one or more catalytically active or inactive materials, synthetic or naturally occurring molecular sieves, or inorganic materials selected from clays, silica, or metal oxides.

2. The catalyst of claim 1, wherein the molecular sieve has, in its as-synthesized form, an X-ray diffraction pattern substantially as shown in the following Table:

| 2-Theta | d-spacing (nm) | Relative Intensity[b] |
|---|---|---|
| 7.55 ± 0.20 | 1.170 | W |
| 8.71 ± 0.20 | 1.015 | W |
| 12.49 ± 0.20 | 0.708 | W |
| 15.12 ± 0.20 | 0.586 | W |
| 21.18 ± 0.20 | 0.419 | VS |
| 22.82 ± 0.20 | 0.390 | VS |
| 24.62 ± 0.20 | 0.361 | W |

[b] W = weak (>0 to ≤ 20);
M = medium (>20 to ≤ 40);
S = strong (>40 to ≤ 60);
VS = very strong (>60 to ≤ 100).

3. The catalyst of claim 1, wherein the molecular sieve has a silicon oxide to aluminum oxide mole ratio of 40 to 220.

4. The catalyst of claim 1, wherein the molecular sieve has a silicon oxide to aluminum oxide mole ratio of 70 to 160.

5. The catalyst of claim 1, wherein the molecular sieve comprises at least 80% polytype 6 of the total ZSM-48-type material present in the product.

6. The catalyst of claim 1, wherein the molecular sieve comprises between 0.1 and 2 wt. % EU-1.

7. The catalyst of claim 1, wherein the crystallites collectively have an average aspect ratio of between 1 and 5.

8. The catalyst of claim 1, wherein the molecular sieve comprises at least 90% polytype 6 of the total ZSM-48-type material present in the product.

9. The catalyst of claim 1, wherein the crystallites collectively have an average aspect ratio of between 1 and 3.

10. The catalyst of claim 1, wherein the modifying metal comprises nickel, platinum, palladium, or a combination thereof.

11. A process for converting hydrocarbons, comprising contacting a hydrocarbonaceous feed under hydrocarbon converting conditions with the catalyst of claim 1.

12. The catalyst of claim 1, wherein the molecular sieve is prepared from a reaction mixture comprising at least one source of silicon, at least one source of aluminum, at least one source of an element selected from Groups 1 and 2 of the Periodic Table, hydroxide ions, hexamethonium cations, and water; and the reaction mixture is subjected to crystallization conditions sufficient to form crystals of the molecular sieve.

13. The catalyst of claim 1, wherein the molecular sieve is prepared from a reaction mixture comprising, in terms of mole ratios, the following:

| | |
|---|---|
| $SiO_2/Al_2O_3$ | 50-220 |
| $M/SiO_2$ | 0.05-1.0 |
| $Q/SiO_2$ | 0.01-0.2 |
| $OH/SiO_2$ | 0.05-0.4 |
| $H_2O/SiO_2$ | 3-100 | wherein M is selected from the group consisting of elements from Groups 1 and 2 of the Periodic Table; and Q is a hexamethonium cation.

14. The catalyst of claim 1, wherein the molecular sieve is prepared from a reaction mixture comprising, in terms of mole ratios, the following:

| | |
|---|---|
| $SiO_2/Al_2O_3$ | 85-180 |
| $M/SiO_2$ | 0.1-0.8 |
| $Q/SiO_2$ | 0.02-0.1 |
| $OH/SiO_2$ | 0.10-0.3 |
| $H_2O/SiO_2$ | 10-50 | wherein M is selected from the group consisting of elements from Groups 1 and 2 of the Periodic Table; and Q is a hexamethonium cation.

15. The catalyst of claim 1, wherein the molecular sieve is combined with a matrix material prior to loading with one or more Groups 8 to 10 metals.

* * * * *